United States Patent [19]

Gross et al.

[11] 4,351,799

[45] Sep. 28, 1982

[54] MICROMETERING LIQUID SAMPLE DISPENSER

[76] Inventors: Valery N. Gross, ulitsa Luganskogo, 73; Evgeny V. Kozhanov, ulitsa Masanchi, 79 "B", kv. 17; Vyacheslav D. Stupnik, ulitsa Transportnaya, 44; Vladimir V. Valov, ulitsa Astronomicheskaya, 82, kv. 37, all of Alma-Ata, U.S.S.R.

[21] Appl. No.: 283,786

[22] Filed: Jul. 15, 1981

[51] Int. Cl.³ .............................................. G01N 1/14
[52] U.S. Cl. ...................................... 422/63; 422/64; 422/67; 422/100
[58] Field of Search ....................... 422/63, 64, 65, 67, 422/100, 81, 103

[56] References Cited

U.S. PATENT DOCUMENTS

| | | | |
|---|---|---|---|
| 3,193,358 | 7/1965 | Baruch | 422/64 |
| 4,087,248 | 5/1978 | Miles | 422/63 X |
| 4,106,911 | 8/1978 | Marcelli | 422/63 |
| 4,276,048 | 6/1981 | Leaback | 422/65 X |

Primary Examiner—Ronald E. Serwin

Attorney, Agent, or Firm—Steinberg & Raskin

[57] ABSTRACT

A micrometering liquid sample dispenser for dispensing several sample liquids into a test tube comprises syringe samplers arranged on a stand and equal in number to the number of sample liquids, the syringe samplers being provided with pipes or hoses for conveying the metered sample liquids to the test tube, the stand being kinematically linked with a sample volume regulator. The apparatus is further provided with a control unit incorporating a sample volume and timing setter the outputs of which are connected to the sample volume regulator, to a drive for step-by-step rotation of the test tube tray and to a drive for reciprocating the ends of the sample liquid dispensing pipes. Each of the syringe samplers is provided with means for locking the piston rod thereof to effect a programmable liquid sample metering, the lock means being electrically connected with a corresponding output of the sample volume and timing setter. Also, there is a provision for a holder to hold the ends of the sample liquid dispensing pipes to dispense the sample liquid into the test tube, the holder being adapted to hydraulically communicate with the outlets of the syringe samplers via three-way valves.

5 Claims, 8 Drawing Figures

MICROMETERING LIQUID SAMPLE DISPENSER

INDUSTRIAL APPLICABILITY

The present invention relates to apparatus for dispensing measured volumes of liquids, and more particularly to a micrometering liquid sample dispenser.

The apparatus according to the invention can find application in chemical, biochemical, molecular biological, microbiological, selective and medical examinations, as well as for conducting clinical analyses. Also, it can be employed with advantage in the chemical, pharmaceutical, radiochemical and microbiological industries for the preparation of multicomponent mixtures from solutions of highly pure substances in microliter volumes.

BACKGROUND OF THE INVENTION

The advent of novel and highly promising chemical and biochemical methods of analysis which have found application on an ever increasing scale in recent years in medicine and industry for research purposes calls for the provision of apparatus capable of taking very small measured volumes of several sample liquids to be dispensed into a single test tube. These methods include biochemical modelling and genetic engineering, immunology, enzymological and bioluminescent methods, as well as kinetic methods of clinical analysis. The methods are based on the preparation of a sample of a multicomponent mixture of solutions of high purity. To this end, very small measured volumes of sample liquids are dispensed into and simultaneously mixed in a single test tube. Therewith, the volumes of each of the measured sample solutions, depending on the specific aims of the analysis, vary within two samples, whereas the measured volumes of the solutions are dispensed and mixed either simultaneously, or by a controllable delay in dispensing of one or more components thereof. The latter affords not only to improve the accuracy and reproducibility of the analyses, but also to obtain added information on the character of the reactions constituting the method resulting in new data relating to the substances under analysis.

For example, in enzymological and bioluminescent methods, as well as in the methods of biochemical modelling and genetic engineering, determination of the kinetic parameters of the analytical reactions enables to evaluate not only the quantity of the biomolecules, but also the functional properties of the molecules and those of the activation centers thereof. On the other hand, in all of the above stated analytical methods each of the substances dispensed into the test tube features a concentration exceeding the value required for reaction to proceed, this being necessitated by the concentration to be reduced to a normal value in the course of adding other sample components. Rapid and simultaneous mixing of all sample components may, therefore, prove a decisive factor for a majority of analytical reactions to take place. This can be accounted for by the fact that many biologically active molecules subject to analysis tend to irrevocably alter their structure and lose the functional activity at high concentrations of a number of salts, although small concentrations of the latter are an essential factor for initiating the reaction.

A device for micrometering several sample liquids to be dispensed into a single test tube must therefore provide, in accordance with a programmable analysis, automatic variations in the volume and time of liquid sample dispensing along each of the channels, as well as high reproducibility and accuracy of dispensing.

When dispensing liquid samples measured in microliters, it is important that a provision be made for separating from the end of a sample liquid conveying tube a measure of liquid in volume by far less than a drop thereof. Incomplete separation of the sample liquid from the end of the conveying tube may reduce severalfold the accuracy of metering. Therefore, along with the provision of a high precision sample metering means, it is just as important to provide a liquid sample dispensing assembly that would meet the above requirement.

An advantage of the above methods resides in their high sensitivity, which to a large extent depends on the purity of reagents used for analysis. For example, the bioluminescent method enables to detect $10^{-13}$ of a gram of substance. Conversely, the presence in the sample under analysis of even negligible quantities (in the order of tenths of one percent) of admixtures including the solutions used for analysis, reduces the sensitivity of the method by several orders of magnitude. This requirement to maintain the purity of the solutions relates in equal measure both to the measured samples and to the initial sample liquids, which imposes additional limitations on the construction of the sample conveying assembly.

As has been stated above, in the multiple-component reactions use is made of solutions with high concentration of substance therein. This is explained not only by the need to dilute the solution in the course of the preparation of a multicomponent mixture, but also by the necessity to obtain a highly reactive mixture. The latter applies mostly to the analysis of biomolecules. Therefore, it is almost always undesirable to dilute the sampled solution by adding water or flushing fluids used for flushing the pipes and metering vessels for changing the sample liquids.

The use in said methods of highly pure and costly reagents poses another requirement to devices for micrometering sample liquids, viz. the sample liquids must remain in the interior of pipes, syringes and containers after the sample liquid have been measured.

There is known a micrometering sampler (cf. USSR Inventor's Certificate No. 463,027, IPC G 01 N 1/10, G 01 F 11/06, published Mar. 5, 1975) comprising piston-and-cylinder syringes secured on a bracket with the piston rods thereof extending upwards to cooperate with a common driver. The bracket also mounts adjusting screws for presetting the volume of liquid being sampled.

With the pistons of the syringes in the downmost position, the bracket is manually lowered for the needles of the syringes to enter vessels containing sample liquids. The driver is then raised to draw into the syringes the sample liquids, whereafter the bracket is raised to replace the sample containers with empty test tubes to receive the thus sampled liquid. The bracket is then again lowered for the measured sample liquid to fill the test tubes by pressing the driver.

Insufficient automation in the above device determines the low efficiency of dispensing several sample liquids into a test tube. Another disadvantage of the apparatus resudes in a low accuracy of liquid metering because the syringes are positioned with their piston rods extending upwards, which impedes the removal of air from the interior thereof during drawing in the sample liquid.

Flushing the interior of the syringes subsequent to each dispensing operation reduces further the efficiency of the apparatus, while the flushing fluid remaining in the interior and the walls of the syringes and needles thereof result in dilution of the sampled liquid. In cases where dilution is inadmissible, the needles are not flushed which in turn leads to cross contamination of the sample liquid and measured samples thereof.

Also known is a micromeasuring liquid sampler (cf. U.S. Pat. No. 3,991,616, Cl. B 01 L 3/02, published Nov. 16, 1976) comprising a syringe with the piston rod thereof extending upwards and having several openings to hold pipes therein. Each of the pipes is made up of three sections fabricated respectively from polyamide, plasticized polyvinyl chloride and stainless steel, the polyamide sections being fixedly secured in the openings of the syringe. The plasticized polyvinyl chloride sections in conjunction with solenoid controlled pipe pinching means form a shut off unit of each of the pipes. The steel sections are immersed in liquid sample containing vessels. A container is provided for a flushing fluid, while a test tube is further provided for receiving measured quantities of the sample liquids. The piston rod is connected to a step-by-step drive to impart reciprocations thereto.

During the upward movement of the piston, all the pipes are closed except one intended to convey either any of the sample liquids or the flushing fluid. The sample liquid flows along this pipe into the interior of the syringe. During the downward movement of the piston all the pipes are closed except one intended for dispensing the sample liquid into the test tube. The flushing fluid is the last to be conveyed to wash the interior of the syringe.

A disadvantage of the above apparatus resides in that removal of air from the interior of the syringe is complicated due to the piston rods being positioned to extend upwards; such an arrangement of the piston rods results in more time to be consumed for making the apparatus ready to operate and leads to considerable analytical errors because of the air bubbles formed during the suction of viscous gas-containing liquids and remaining in the interior of the syringe.

Conveying the sample liquids in succession through one syringe makes it necessary to flush the syringe subsequent to each sample preparation, while in order to completely clean the interior of the syringe, the latter should be flushed at least 10 times, which is described in detail in Analytical Biochemistry, vol. 86, 1978, pp. 1-20 - Christian Stahly, John H. Wharton, Hans Noll "A Computer Controlled Multichannel Micropipetter".

On the one hand, this limits the efficiency of the micromeasuring liquid sampler, while on the other it becomes a source of cross contamination, since the experimentally found requirement to flush the sampler ten times is sometimes not sufficient to completely clean the sampler. The foregoing does not permit to obtain samples free from the flushing fluid, which in turn results in reduced concentration of the sample components and lower the reactivity thereof.

Also, for successive dispensing of all the solutions of the multicomponent sample by one syringe sampler, the need to take into consideration the volume of sample liquid in the pipe and make corrections due to free play in the connections of the drive for reciprocating the piston rod add to inconveniencies for the operator.

Further known is a liquid sampler comprising syringes equal in number to the number of sample liquids being measured and provided with pipes for conveying and dispensing the liquids into a test tube arranged on a tray, the syringes being secured in a stand kinematically linked with a sample volume regulator in the form of a drive for reciprocating the pistons of the syringes relative to the cylinders thereof, the drive being electrically connected to a sample volume and timing setter forming part of a control unit, the control unit being electrically wired with another drive means for imparting reciprocations to the ends of the sample conveying pipes (cf. brochure "Sample Processor" of the Kone Company, Finland).

The outlets of the syringes are connected by pipes to respective probes secured on a bracket linked with a drive for imparting a step-by-step vertical and horizontal movement thereto. The position of each probe is such that it corresponds to the position of a respective test tube of three rows of tubes equal in number to the number of the sample liquids. Arranged horizontally under the bracket in the path of travel thereof are the tube carrying tray, vessels containing the sample liquids being metered and a flushing fluid container having a means for mechanically cleaning the probes.

The apparatus is controlled by a microprocessor. Upon depressing respective buttons, the bracket is caused to move horizontally toward the flushing fluid container to be lowered in the downmost position, whereby the syringes, pipes and probes are filled with the flushing fluid by several reciprocations of the syringe pistons.

From their downmost position the pistons are moved upwards a distance corresponding to a preselected volume of the first sample liquid. Therewith, the bracket moves upwards and is displaced horizontally toward the first sample liquid to be thereafter lowered into the vessel containing the liquid. The pistons are then moved to their downmost position to draw the sample liquid, after which the bracket is again raised and moved toward the first row of test tubes and lowered to introduce the probes into the test tubes. The pistons are then moved upwards for the first sample liquid to fill the test tubes, whereupon the bracket is raised, moved toward the flushing fluid container and again lowered. The upward movement of the pistons causes a portion of the flushing fluid to be forced out of the probes. The bracket is then raised, which is accompanied by the probes passing through the mechanical probe cleaning means, whereafter the sampling and dispensing cycle is repeated for the second sample liquid etc., depending on the number of sample liquid employed.

However, the drive for reciprocating the piston rods of the syringes fails to permit variations in the amount of each of the sample liquids being drawn thereinto, which substantially restricts the range of application of the apparatus.

Due to all of the piston rods being driven by a common drive, it is impossible to vary the time of dispensing, which in turn impedes the use of the apparatus for conducting kinetic analyses requiring simultaneous dispensing and simultaneous mixing all the liquid sample components. For the same reason, the apparatus cannot be used for a number of analyses of the functionally active biomolecules wherein the effect of high salt concentration is inadmissible, although the salts are necessary for the reaction of the low concentration sample components. Another drawback resides in that the apparatus cannot be used for such analyses which require successive adding the components making up the sample, since the interval between successive dispensing into the sample of two liquids cannot be made less than one dispensing cycle exceeding in this apparatus ten seconds.

Further, some free play may be present in the movable connections between the drive and the piston in the course of reciprocations impairing the accuracy of sampling, the free play being determined by the structural arrangement of the drive for moving the pistons of the syringes, limiting the operating cycle by only one measure of sample liquid being taken.

Due to the volume of the sampled liquid being very small, the drop of liquid may not fall into the test tube, for which reason the end of the probe is introduced directly into the already measured and dispensed liquid. This results in that a portion of the liquid is likely to be carried by the end of the probe, the volume of the thus withdrawn liquid amounting to 30–40 microliters, which is practically equal to the volume of one liquid drop. This is inadmissible for most of the above analyses, because the final sample containing all the measured sample liquids may have the same volume. Therefore, the above apparatus features low accuracy and cannot be used for a number of analyses.

In spite of the provision for the flushing fluid and probe cleaning means, the sample liquids and the measured samples are subject to cross contamination. Further, it is the flushing fluid and the probe cleaning means that cause such a cross contamination. Each operating cycle is accompanied by at least some of measured sample liquid being carried by the probe from the test tube containing the mixture of measured sample into the flushing fluid. As a result, when metering highly concentrated solutions after only several cycles the concentration of the sample substances in the flushing fluid may reach tenths of one percent. Secondly, after each cycle of sample liquid dispensing a small amount of the sample liquid being measured is added to the flushing fluid by the probe, which also leads to a gradual build up therein of the substances diluted in the sample liquids. Thirdly, the mechanical probe cleaning means fails to provide cleaning of the entire surface area of the probe, which results in transfer of the flushing fluid to the measured samples along with all the substances present therein. Besides, the probe cleaning assembly requires accurate alignment of the probes relative thereto.

Filling the flush fluid wetted interiors of the probe and pipes with the sample liquid being measured dilutes the sample liquid during each measuring cycle resulting in less accurate sample liquid metering and errors in subsequent analyses. Dilution of the sample liquid components also brings down the rate of reaction which rules out kinetic analyses to be carried out.

Multiple flushing the outer surfaces of the probes and interior thereof as well as the interior of the sample liquid conveying pipes leads to losses of the sample liquids being measured, which is highly undesirable when analyzing very pure substances. Conversely, flushing is an obligatory operation, since the construction of the sample liquid metering means, the drive thereof and the reciprocating liquid dispensing probes necessitates sequential metering different sample liquids by each of the syringes, which in turn requires flushing respective pipes during each sample metering cycle. Also, the flushing fluid is liable to penetrate the sample liquid due to incomplete cleaning of the probes. Therefore, the remainder of the sample liquids in the containers are not suitable for further use after a series of analyses have been conducted, which likewise results in losses of the sample liquids.

SUMMARY OF THE INVENTION

It is an object of the present invention to provide an apparatus for micrometering sample liquids which would afford to vary the volume of each of the sample liquids being metered along with the time of dispensing thereof and to improve the accuracy of metering.

Another object is to prevent losses of the sample liquids being metered.

Still another object is to obviate the need for flushing the sample metering means and the sample conveying pipes in the course of sample metering.

Yet another object is to provide improved mixing of the metered sample liquids in a test tube.

The objects are attained by that in a micrometering liquid sample dispenser comprising syringe samplers equal in number to the number of sample liquids being metered and dispensed and having pipes for conveying the sample liquids into an appropriate test tube secured in a test tube tray, the syringe samplers being located in a stand kinematically linked with a sample volume regulator in the form of a drive for relative reciprocating displacement of pistons and cylinders of the syringe samplers electrically connected to a sample volume and timing setter forming part of a control unit, an output of which is wired with a drive for reciprocating the ends of the sample liquid dispensing pipes, according to the invention, each of the syringe samplers is provided with a means for locking the piston rod thereof to effect a programmable liquid sample metering, the locking means being electrically connected with corresponding outputs of the sample volume and timing setter, whereas there are further provided a holder intended to hold the ends of the sample liquid dispensing pipes for programmably dispensing the sample liquids into the test tube and a drive for a step-by-step rotation of the test tube tray electrically connected with an output of the control unit.

Preferably, each of the means for locking the piston rod of the syringe sampler is provided with a solenoid and an arm in the form of a plate of varying thickness, one end of which is fixedly secured to a lug, while another end is adapted to cooperate with a core of the solenoid electrically connected with the corresponding output of the sample volume and timing setter, the plate and lug having congruent grooves to lockingly engage with the piston rod of the piston, the diameter of the congruent grooves being essentially less than the cross-section of the piston rod.

Advantageously, the pipe end holder comprises a base having a central bore and slots equal in number to the number of sample liquids being metered and dispensed, the slots receiving fixedly secured therein portions of the pipes for conveying the sample liquids being metered, the base being rigidly affixed to a bracket of the drive for reciprocating the ends of the sample liquid dispensing pipes, a pressurized air supply pipe slidably secured in the central bore of the base, a conical sleeve affixed to the end of the pressurized air supply pipe and having peripheral openings for the ends of the sample liquid dispensing pipes to fit loosely therein, the radial distance between the openings and the axis of the sleeve being essentially greater than the radial distance between the axis of the base and the slots, and an arched plate to serve as a stop or rest having a bore with the pressurized air pipe fixedly secured therein, the end of the pressurized air pipe being arranged at an angle to the axis thereof to facilitate the breaking away of the sample liquid drops from the extremities of the sample liquid dispensing pipes.

Advantageously, the interior volume of a section of at least one of the liquid dispensing pipes is adapted to equal the maximum displacement volume of the corresponding syringe sampler, this volume being proportional to the length of stroke of the piston rod of the syringe piston.

Preferably, the liquid sample volume and timing setter comprises a rotating drive, a drum carrying a program punch card, the drum being secured on a shaft of the drive, a setting pulse transducer, a reference pulse transducer mounted on a guide for axial movement relative to the drum, setting pulse counters, a switching unit for successively connecting outputs of the setting pulse transducer and reference pulse transducer to the setting pulse counters, a comparator circuit, inputs of which are connected with the corresponding setting pulse counters, a counter of revolutions made by the drive for reciprocating the pistons of the syringe samplers relative to the cylinders thereof, the output of the revolution counter being connected to corresponding inputs of the comparator, the outputs of which are connected to the solenoids of the respective means for locking the piston rods of the syringe samplers, a time meter connected by the output thereof to inputs of the comparator circuit, and a time setter for liquid sample metering and dispensing, the output of which is connected to input of the time meter; the control unit incorporating a circuit for synchronized engagement of the sample volume regulator and the drives of the apparatus, lock means positioning circuit and pick ups for monitoring the positions of the piston rod lock means the pick ups being located in the lock means and electrically connected to corresponding inputs of the lock means positioning circuit having an output thereof connected to the input of the circuit for synchronized engagement of the drives of the apparatus.

The herein proposed apparatus makes it possible to vary the volume of each of the sample liquids being concurrently metered and the timing thereof thanks to the provision of the means for fixing the piston rods of the sample syringes which are electrically connected with corresponding outputs of the liquid sample volume and timing setter. The apparatus also affords simultaneous dispensing of metered volumes of various sample liquids into a single test tube through the employment of a holder for holding the ends of the sample conveying pipes. Cross contamination of the sample liquids has been prevented by using a jet of pressurized air to break the drops of sample liquids from the extremities of the sample dispensing pipes, which obviates the need for immersing these ends in the measured and dispensed sample liquids held in the test tubes. The construction of the apparatus further makes it superfluous to flush the samplers and pipes subsequent to each liquid sample metering operation. The jet of pressurized air facilitates mixing the liquids making up the sample in the test tube.

BRIEF DESCRIPTION OF THE DRAWINGS

The invention will now be described in greater detail with reference to specific embodiments thereof taken in conjunction with the accompanying drawings, in which:

FIG. 3 (a, b) is a view of a holder of the ends of the pipes for conveying a sample liquid showing also a pressurized air pipe;

DETAILED DESCRIPTION OF THE INVENTION

Figure 1:
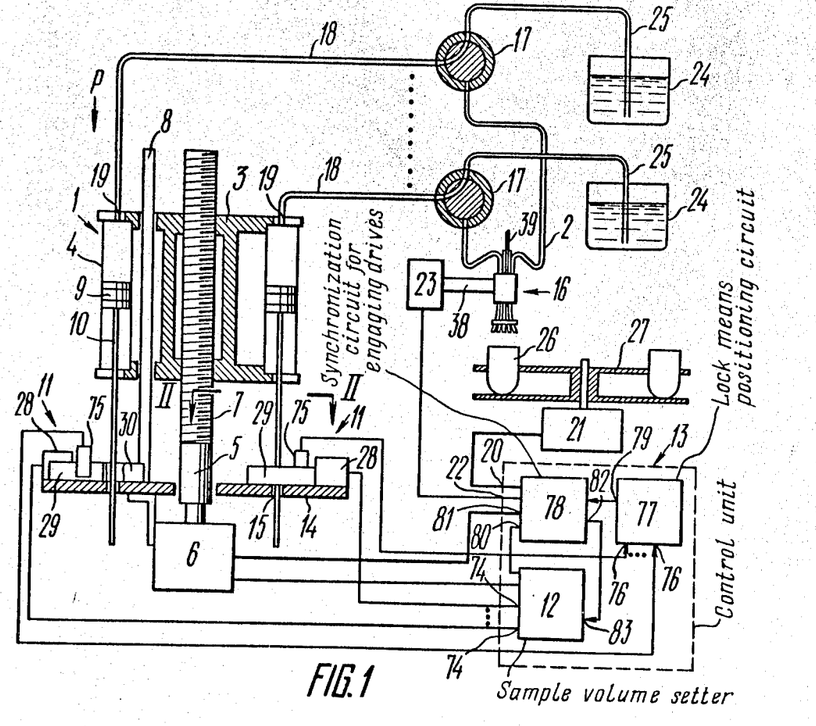
FIG. 1 shows a schematic diagram of a micrometering liquid sample dispenser according to the invention and a block diagram of the control unit thereof.

With reference to FIG. 1, a micrometering liquid sample dispenser according to the invention comprises syringe samplers generally indicated by 1 equal in number to the number of sample liquids being metered and provided with pipes or hoses 2 for conveying the liquids to a test tube. The syringe samplers 1 are mounted on a stand 3 having the form of a cylinder with projecting flanges wherebetween there are secured cylinders 4 of the syringe samplers 1. The stand 3 is mounted on a shaft or post 5 of a sample volume regulator 6 in the form of a drive for relative reciprocating displacement of pistons and cylinders of the syringe samplers. The shaft or post 5 is threaded at 7 for effecting displacement of the stand 3 by virtue of female threads provided therein. The stand 3 moves along a guide bar 8 intended to prevent rotation of the stand 3.

Inside the cylinders 4 are pistons 9 with piston rods 10. The device also comprises means 11 for locking the piston rods for programmably measuring samples, the lock means 11 being electrically connected with appropriate outputs of means 12 for setting the volume of sample liquid being measured and the time for dispensing thereof to the test tube, the means 12 forming part of a control unit 13. The lock means 11 are affixed to a platform 14 which is rigidly connected with the guide bar 8 and the sample volume regulator 6. Provided for free movement of the piston rods 10 in the platform 14 are openings 15.

The apparatus further comprises a holder 16 for holding the end portions of tubes carrying the sampled liquids and programmable dispensing thereof into a test tube, the holder being connected by pipes 2 via corresponding three-way valves 17 and pipes 18 with outlets 19 of the syringe samplers 1.

Output 20 of the control unit 13 is connected to a drive 21 for imparting a step-by-step rotational movement to a test tube tray 27, while an output 22 thereof is connected to a drive 23 for reciprocating the ends of the tubes dispensing the sampled liquids.

Accommodated in containers 24 are sample liquids to be metered and dispensed. The containers 24 communicate with three-way valves 17 by way of pipes 25.

The measured liquid samples are dispensed into test tubes 26 carried by the tube tray 27 which is rotated by a step-by-step drive 21.

Figure 2:
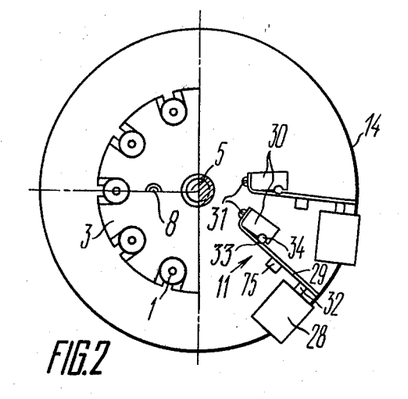
FIG. 2 illustrates a section taken along the line II—II of FIG. 1 showing by way of example only two lock means (to the right of the center line), and a view taken along the arrow P of FIG. 1 (to the left of the center line)

The locks 11 and syringes 1 (FIG. 2) are positioned symmetrically on the platform 14.

The lock means 11 for locking the piston rod of the syringe sampler 1 comprises a solenoid 28, an arm 29 in the form of a resilient plate of varying thickness, one end of which is fixed to a lug 30 by a screw 31, another end thereof being adapted to cooperate with a core 32 of the solenoid 28. The solenoid 28 (FIG. 1) is electrically connected to an appropriate output of the sample volume setting and timing block 12. The resilient plate 29 and the lug 30 (FIG. 2) have congruent grooves 33 and 34, respectively, to receive the piston rod 10 (FIG. 1), the diameter of the two grooves being somewhat less than the cross-sectional diameter of the piston rod 10.

Figure 3A:
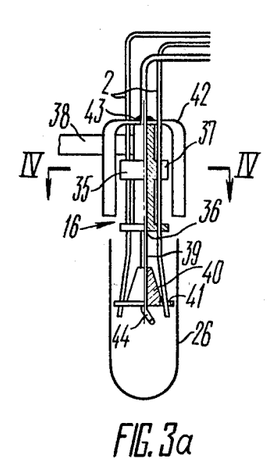
Figure 4:
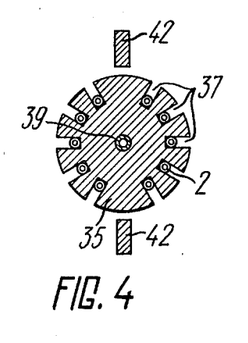
FIG. 4 is a section taken along the line IV—IV of FIG. 3.

The pipe end holder 16 (FIGS. 3-a,b and 4) comprises a base 35 having a central bore 36 and slots 37 corresponding in number to the number of liquids being sampled. The slots 37 accommodate fixedly secured therein pipes 2 for conveying the liquids being dispensed. The base 35 is fixedly secured to a bracket 38 of the drive 23 (FIG. 1) for reciprocating the end portions of the pipes 2. Movably secured in the central bore 36 of the base 35 is a pressurized air pipe 39, the end of said pipe carrying rigidly secured thereto a conical sleeve 40 having openings 41 with the ends of the pipes 2 loosely fitted therein. The distance between the axis of the sleeve and the radial openings 41 is essentially greater than the distance between the axis of the base 35 and the slots 37.

Figure 3B:
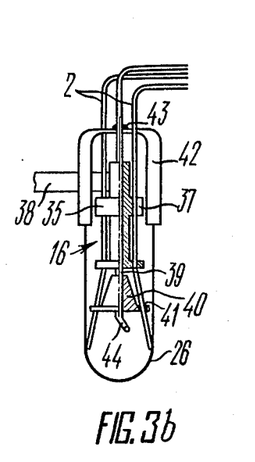

Rigidly fixed on the pressurized air pipe 39 is a curved or arched plate 42 serving as a rest or stop and having a bore 43 for receiving the pipe 39, for more convenience the plate 42 (FIGS. 3a and 3b) being turned 90°. End 44 of the pressurized air pipe 39 is bent or crimped relative to the axis thereof to cause the drops of sample liquid to break away from the extremities of the pipes 2 to fall into the test tube 26. The slots 37 are arranged symmetrically in the base 35.

A section 45 of the pipe 2 for conveying the liquid sample to be dispensed has the form of a coil the interior volume of which is essentially equal to the displacement volume of the corresponding syringe sampler 1.

The sample volume setting and timing block 12 comprises a rotating drive 47 (FIG. 6) secured on a base plate 46, the drive 47 having a shaft 48 with a cylinder or drum 49 fixedly secured thereon. The drum 49 accommodates a sample program punch card 50. The base plate 46 mounts a setting pulse transducer 51 and a threaded shaft 53 having a drive means 52 therefor. Adapted to threadingly engage with the shaft 53 is a reference pulse transducer 54 capable of displacement along a guide 55. The setting block 12 further comprises setting pulse counters 56 equal in number to the number of the syringe samplers 1 and controllable by sample volume reference pulses received from the transducer 54; it also comprises setting pulse counters 57 likewise equal in number to the number of the syringe samplers 1 and controllable by sample timing reference pulses. There are further provided a switching unit 58 to effect successive connections of the outputs of the setting pulse transducer 51 and the reference pulse transducer 54 to the setting pulse counters, and a comparator circuit 59.

Figure 6:
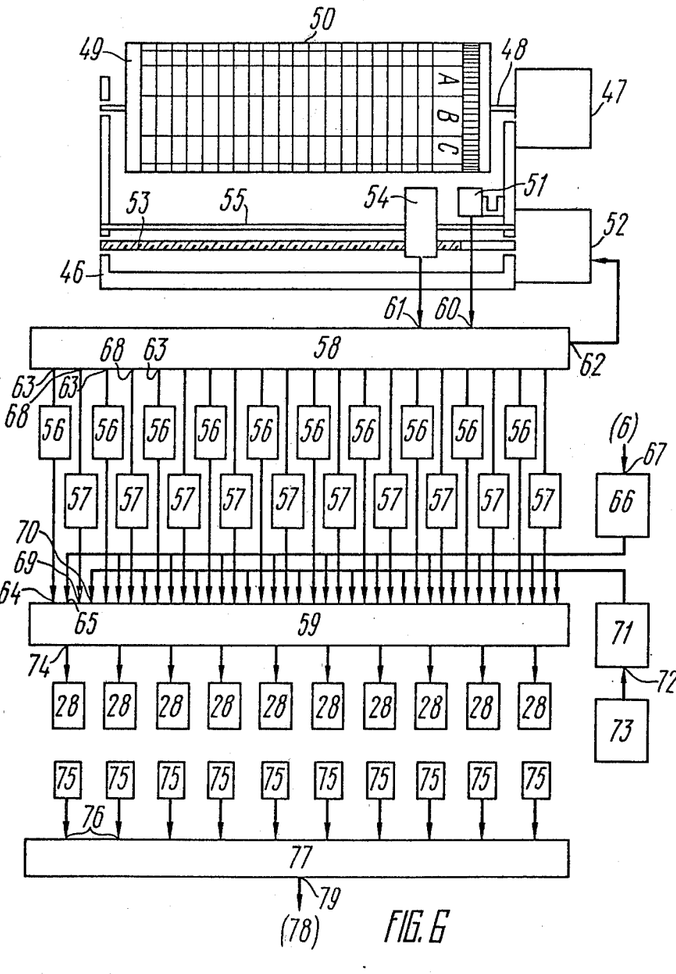
FIG. 6 is a block diagram of a sample volume and timing setter according to the invention.

The setting pulse transducer 51 is connected to input 60 of the switching unit 58, another input 61 thereof being connected to the reference pulse transducer 54.

Output 62 of the switching unit 58 is connected to the input of the drive means 52 for imparting rotation to the shaft 53 to effect a step-by-step displacement of the reference pulse transducer 54. Outputs 63 of the switching unit 58 are connected to inputs of the setting pulse counters 56, whereas outputs of the latter are connected to inputs 64 of the comparator circuit 59. Other inputs 65 of the circuit 59 are connected with outputs of a revolution counter 66 of the drive for reciprocating displacement of the pistons relative to the cylinders of the syringe samplers 1. Input 67 of the revolution counter 66, which is also the input of the setting block 12 (FIG. 1), is connected with the output of the sample volume regulator 6.

Outputs 68 (FIG. 6) of the switching unit 58 are connected to the inputs of the setting pulse counters 57, the outputs of the latter being in turn connected to inputs 69 of the comparator circuit 59. Other inputs 70 of the circuit 59 are connected to the output of time meter 71, input 72 of which is wired with a sample timing setter 73.

Outputs 74 of the comparator circuit 59 are connected to the solenoids 29 of the lock means 11; the lock means 11 carry lock means position pick ups 75 with outputs thereof connected to inputs 76 of the lock means positioning circuit 77.

The control unit 13 (FIG. 1) comprises a circuit 78 for synchronizing the engagement of the sample volume regulator 6 and the drives 21 and 23, input of the above circuit 78 being connected with output 79 of the lock means positioning circuit 77. Outputs 80 and 81 of the circuit 78 are connected respectively to the input of the setter 12 for synchronized actuation and disengagement of the drive 52 rotating the shaft 53 and to the input of the regulator 6 for synchronous engagement and disengagement of the drive for relative reciprocating displacement of the pistons and cylinders of the syringe samplers. The outputs of the synchronization circuit 78 are at the same time intended to serve as the outputs 20 and 22 of the control unit 13. Output 82 of the synchronization circuit 78 is wired with input 83 of the setter 12.

Figure 7:
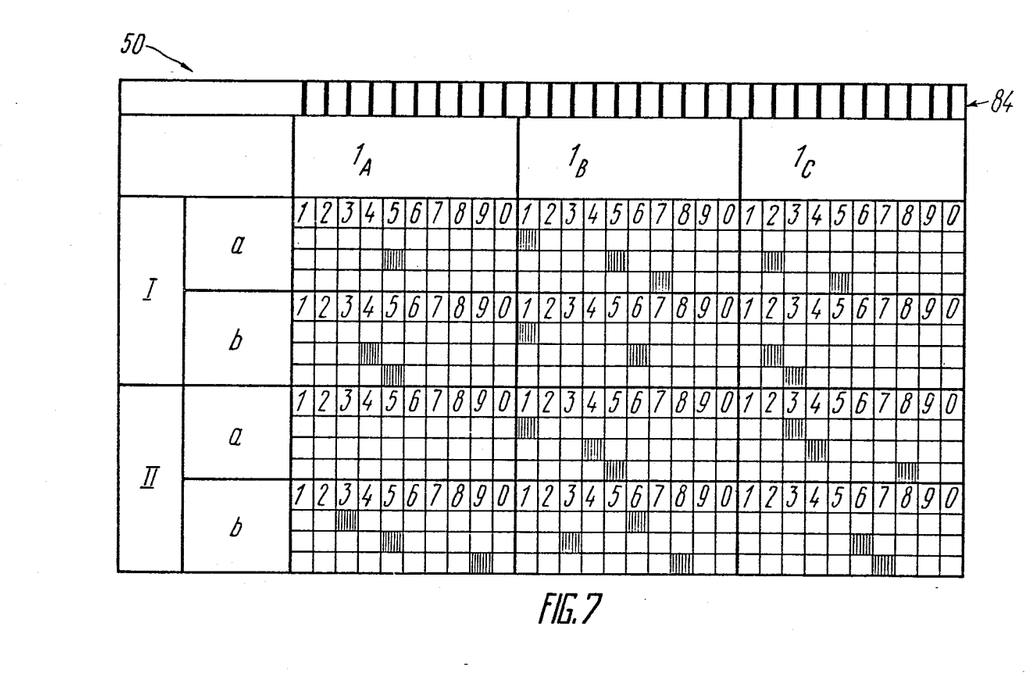
FIG. 7 shows a punch card carrying a program for conveying the sample liquids.

With reference to FIG. 7, the punch card 50 is made up of columns $1_A$, $1_B$ and $1_C$ to correspond to the samplers with liquids A, B, and C being sampled, while rows I and II correspond to a preset mode of sampling. Each of the rows I and II in turn is divided into two coding lines a and b intended for setting the measured volume of liquid to be sampled and timing the moment of sampling, respectively.

Each of the thus formed rectangulars is in turn broken into 10 subcolumns designated by 1, 2, 3, 4, 5, 6, 7, 8, 9 and 0 and three sublines corresponding either to the maximum volume of sample or to the maximum delay time of sampling. The intersection of the subcolumns and sublines form a network for positioning code marks. In the modification described herein each subline corresponds to a decimal number representation system. The punch card 50 also comprises a line 84 carrying coding masks.

The micrometering liquid sample dispenser according to the invention operates in the following manner.

Applied to the punch card 50 (FIG. 7) are coding or reference marks arranged in the squares corresponding to the volume of sample to be measured, whereafter the punch card 50 is secured on the drum 49 of the setter 12 (FIG. 1).

In the position of the valves 17 as seen best in FIG. 1, a measured volume of sample liquid is drawn from the containers 24 into the syringe samplers 1. To this end, locking the piston rods of the samplers 1 is effected by causing the arm 29 (FIG. 2) to press against the lug 30 by the core 32 upon actuating the solenoid 28. In a position wherein the tubes 18 and 25 communicate, the sample liquids are conveyed simultaneously to the syringe samplers 1. The valves 17 are turned in a position wherein the pipes 2 and 18 communicate and the pipes 2 are then filled with the sample liquids.

Upon starting the apparatus, the drive 47 of the drum 49 is also energized and remains energized throughout its operation. The rotation of the drum 49 with the punch card secured thereon causes the transducer 51 to convert light pulses received from the setting code marks 84 into electric pulses, wherein the transducer 54 similarly converts light pulses from the reference code marks.

Simultaneous dispensing of the sampled liquids is effected as follows.

The electric pulses produced by the transducers 51 and 54 are directed to the inputs 60 and 61, respectively, of the switching unit 58 which effects consecutive switching of the setting pulse transducer 51 and the transducer 54 of reference pulses received from the marks of the line a intended for setting the volume of sample being measured to the inputs of the counters 56 from the outputs 63 of the switching unit 58. Therewith, each of the counters 56 stores digitally and decimally the values of measured volumes of each of the sample liquids A, B and C being dispensed for a first mode of dispensing which determines the start of dispensing cycle of each sample.

From the output of the synchronization circuit 78 a signal is fed to the output 22 of the control unit 13 for actuating the drive 23 of the pipe end holder 16, the latter descending into the test tube 26 and introducing therein the ends of the pipes 2.

When the plate 42 (FIG. 3b) rests against the edge of the test tube 26, the downward movement of the pipe 39 and the conical sleeve 40 is halted, while the same downward movement of the base 35 continues. As a result of the lower portion of the base 35 moving toward the conical sleeve 40, the ends of the pipe 2 tend to touch against the walls of the test tube 26.

Upon the base 35 reaching its lowermost position, a signal is fed from the output 82 of the synchronization circuit 78 to the input 83 of the setter 12 and further to the outputs 74 thereof to actuate the solenoids 28. This results in locking engagement of the piston rods 10. The pick ups 75 then respond sending signals to the inputs 76 of the circuit 77 for monitoring the position of the lock means 11. The output 79 of the circuit 77 signals to the input of the synchronization circuit 78, while the output 81 thereof sends a signal for actuating the drive for relative reciprocating displacement of the piston rods of the syringe samplers 1.

Rotation of the shaft or post 5 causes the stand 3 to move downwards along the guide bar 8, whereby the measured sample liquids are forced from the cylinders of the samplers 1 into the tubes 18 to be conveyed via the valves 17 and pipes or hoses 2 onto the walls of the test tubes 26, at which time pulses start to appear in the sample volume regulator 6 to enter the input 67 of the counter 66 corresponding to the number of revolutions made by the drive of the syringe samplers 1.

When the signals delivered to the inputs 64, 65 of the comparator circuit 59 coincide, a signal is developed in the output 74 for deenergizing the corresponding solenoid 28, whereby the lock means 11 releases the piston rod of the corresponding syringe sample 1. Therewith the arm 29 of the lock means 11 acts to move the core 32 into the initial position by virtue of the plate resiliency thereby releasing the rod 10. As a result, the supply of the sample liquid being measured is stopped which determines the amount of sample liquid conveyed to the test tube 26. Micrometering of sample liquids by all the syringe samplers is effected in a similar manner.

After the measured quantities of all the sample liquids A, B and C have been taken by the syringe samplers 1, a signal is produced at the output 79 of the circuit 77 for monitoring the position of the lock means corresponding to the initial position of all the lock means 11. This signal acts to deenergize the drive of the samplers and actuate a compressor (not shown). By means of a jet of pressurized air escaping from the end 44 (FIG. 3) of the pipe 39, the drops of sample liquid are broken away from the extremities of the pipes 2. Simultaneously, the air jet stirs the sample liquids in the test tube 26. The end of the process of sampling and dispensing is determined by this breaking away of the final drops of the sample liquids from the extremities of the pipes 2 and the resultant measures of the sample liquids thus obtained in the test tube.

After a certain predetermined period of time, the compressor is stopped and the output 22 of the control unit 13 sends a signal to actuate the reciprocating drive 23. The holder 16 is then raised to thereby retract the ends of the pipes 2 from the test tube 26 into the initial upmost position. The start of such a retraction is characterized by the conical sleeve 40 tending to remain in position, while the base 35 moves upwards. Therewith, the ends of the pipes 2 come out of touch with the walls of the test tube 26 to assume the initial position.

Upon the holder 16 reaching its upmost position, the output 20 of the synchronization circuit 78 delivers a signal to the input of the step-by-step drive 21 of the test tube tray to turn the tray 27 and move a subsequent empty and clean test tube directly under the holder 16 to correspond to a second mode of sample liquids micrometering; this is followed by a signal for the energization of the step-by-step drive 52 to effect a stepped movement of the transducer 54 escaping from the output 80 of the synchronization circuit 78 to enter the input of the setter 12. The transducer 54 moves to assume a position corresponding to the line 84 of reference marks to effect the second mode of sample liquids micrometering. The above cycle is then recommenced for a second liquid sample to be dispensed.

A change in the timing of the measured sample liquids to be supplied is effected in the following manner.

At the start of the liquid sample measuring cycle the electric pulses produced by the transducers 51 and 54 are successively delivered via the switching unit 58 from the outputs 68 to the inputs of the counters 57. Each of the counters 57 stores digitally the delay time relative to the beginning of metering of every sample liquid.

As the base 35 assumes its downmost position, a signal for actuating the solenoids 28 to lock the piston rods 10 is supplied only to the solenoids 28 of the lock means 11 of those syringe samplers 1 for which, according to the program of sampling, the delay time is zero. The moment of locking the piston rods of the rest of the syringe samplers 1, which marks the beginning of the measured supply of the corresponding sample liquids, is determined by the coincidence in the readings of the counters 57 and 71, the corresponding signals being received therefrom by the inputs 69 and 70, respectively, of the comparator circuit 59. Accordingly, the outputs 74 of the circuit 59 receive a signal for actuating the corresponding solenoids 28, which lock the piston rods 10 in position. Other steps of operation are similar to the simultaneous supply of the sample liquids.

Figure 5:
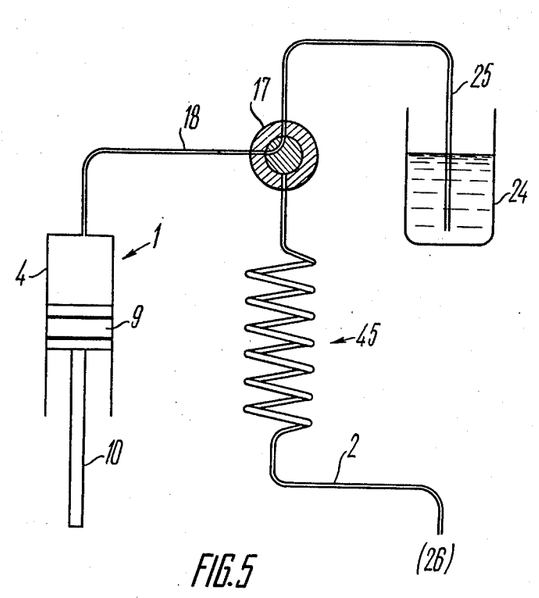
FIG. 5 illustrates passageways along which the sample liquid flows from a syringe sampler via a three-way valve into a test tube.

For a modification of the pipe 2 as shown in FIG. 5 the sample metering is effected in the following manner.

The end of the pipe 2 is separated from the holder 16 to immerse into the sample liquid container 24 to fill with this liquid the pipe 2 up to the valve 17. Therewith, the valve 17 is in a position to communicate the pipes 2 and 18. The valve 17 is then turned to assume the initial position, whereafter the interior of the syringe and that of the pipe 18 are filled with a flushing fluid from a flushing fluid vessel (not shown) by several reciprocations of the piston 9. This is followed by switching the valve 17 in a position communicating the pipes 2 and 18 to thereby force or dispense the sample liquid from the pipe 2.

In the course of such dispensing, an air bubble is present between the sample liquid and the flushing or propulsion fluid to prevent them from intermixing. On forcing the propulsion fluid away from the cylinder of the syringe sampler 1, it is caused to flow along the pipe 18 via the valve 18 and further along the pipe 2. The force or pressure thus produced acts upon the sample liquid in the pipe 2. The volume of the sample liquid forced from the pipe 2 into a test tube corresponds to the volume of the propulsion fluid forced from the syringe sampler 1. Also, the amount of measured volume of the sample liquid is proportional to the length of stroke of the piston rod of the syringe sampler. Due to the aforegoing arrangement of the pipe 2, losses of the liquid being sampled are completely eliminated.

What is claimed is:

1. A micrometering liquid sample dispenser comprising:
    a group of syringe samplers equal in number to the number of sample liquids being metered and dispensed and having cylinders and piston with piston rods;
    pipes for conveying the sample liquids into a test tube, the pipes being equal in number to the number sample liquids and adapted to communicate with outlets of corresponding aforesaid syringe samplers;
    a stand accommodating said syringe samplers;
    a drive for relative reciprocating displacement of the pistons and cylinders of said syringe samplers serving as a sample volume regulator and kinematically linked with said stand;
    a control unit having a set of outputs;
    a sample volume and timing setter incorporated into said control unit and having a set of outputs;
    a drive for step-by-step rotation of a test tube tray having an output connected to a first output of said set of outputs of said control unit;
    a drive for reciprocating the ends of the sample liquid dispensing pipes relative to the test tube, the drive having an output connected to a second output of said set of said control unit;
    a group of piston rod locking means equal in number to the number of said syringe samplers, the locking means being intended for a programmable metering and dispensing the sample liquids and located in close proximity to said piston rods of said syringe samplers;
    outputs of said piston rod lock means connected to said corresponding outputs of said sample volume and timing setter;
    three-way valves equal in number to the number of sample liquids being measured and dispensed adapted to hydraulically communicate said corresponding pipes for conveying the sample liquids into a test tube;
    pipes equal in number to the number of sample liquids;
    containers for the sample liquids; and
    a holder for holding the ends of said pipes for conveying the sample liquid being metered and dispensed to effect a programmable dispensing into a test tube.

2. An apparatus as claimed in claim 1 wherein said lock means for locking the piston rod of said syringe sampler comprises:
    a solenoid connected to a corresponding output of said array of outputs of said sample volume and timing setter, the solenoid having a core;
    a resilient plate of varying thickness serving as an arm, one end of the plate being affixed to a lug, another end thereof being adapted to cooperate with said core of said solenoid; and
    congruent grooves to receive said piston rod provided in said resilient plate and said lug, the diameter of the grooves being essentially less than the cross-section of said piston rod.

3. An apparatus as claimed in claim 1 wherein said holder for holding the ends of pipes for conveying the sample liquid being measured and dispensed into a test tube comprises:
    a base having a central bore and slots equal in number to the number of sample liquids being metered and dispensed;
    portions of said pipes for conveying the sample liquids which are fixedly secured in said slots;
    a bracket of said drive for reciprocating the ends of said sample liquid dispensing pipes having rigidly secured thereto said base;
    a pressurized air supply pipe secured slidably in said central bore of said base;
    a conical sleeve affixed to the end of said pressurized air supply pipe;
    openings in said conical sleeve for the ends of said sample liquid dispensing pipes to fit loosely therein, the radial distance between the openings and the axis of said sleeve being essentially less than the radial distance between the axis of said base and said slots;
    an arched plate serving as a rest and having a bore therein, said pressurized air supply pipe being fixedly secured in said bore; and
    an end of said pressurized air supply pipe, the end being arranged at an angle to the geometrical axis of said holder to facilitate the breaking away of the sample liquid drops from the extremities of said liquid sample dispensing pipes.

4. An apparatus as claimed in claim 1, wherein the interior volume of a section of at least one of said liquid dispensing pipes is adapted to equal the maximum displacement volume of said corresponding syringe sampler.

5. An apparatus as claimed in claim 2 wherein said liquid sample volume and timing setter comprises:

a rotating drive;
a drum secured on a shaft of said rotating drive;
a program punch card arranged on said drum;
a setting pulse transducer having an output;
a guide secured to a base plate of said rotating drive essentially in parallel with the geometrical axis of said shaft of said rotating drive;
a reference pulse transducer mounted on said guide bar for movement axially of said drum and having an output;
a group of setting pulse counters having outputs;
a switching unit for successively connecting said outputs of said setting pulse transducer and said reference pulse transducer to said inputs of setting pulse counters;
a comparator circuit having a first set of inputs connected to said corresponding outputs of said setting pulse counters, a second set of inputs and a set of outputs;
a counter of revolutions made by said drive for reciprocating the pistons of said syringe samplers relative to the cylinders thereof having an output connected with corresponding inputs of said second set of inputs of said comparator circuit;
said outputs of said comparator circuit being connected to said solenoids of said means for locking the piston rods of said syringe samplers;
a time meter having outputs connected to respective inputs of said second set of inputs of said comparator circuit and an output;
a time setter for liquid sample metering having an output connected to said input of said time meter;
said control unit further comprises:
a circuit for synchronized engagement of said drives of the apparatus having an input;
a lock means positioning circuit having a set of inputs and an output, the latter being connected to said input of said circuit for synchronized engagement of said drives of the apparatus; and
pick ups for monitoring the positions of the piston rod lock means located in said lock means and connected to said corresponding inputs of said lock means positioning circuits.

* * * * *